(12) United States Patent
Dion et al.

(10) Patent No.: US 11,317,935 B2
(45) Date of Patent: May 3, 2022

(54) CONNECTOR DEVICE FOR CONNECTING MECHANICAL WAVEGUIDES

(71) Applicant: Les Solutions Medicales Soundbite Inc., Saint-Laurent (CA)

(72) Inventors: Steven Dion, Sherbrooke (CA); Martin Brouillette, Sherbrooke (CA); Louis-Philippe Riel, Montreal (CA)

(73) Assignee: LES SOLUTIONS MEDICALES SOUNDBITE INC., Saint-Laurent (CA)

( * ) Notice: Subject to any disclaimer, the term of this patent is extended or adjusted under 35 U.S.C. 154(b) by 862 days.

(21) Appl. No.: 16/096,178

(22) PCT Filed: Apr. 25, 2017

(86) PCT No.: PCT/IB2017/052388
§ 371 (c)(1),
(2) Date: Oct. 24, 2018

(87) PCT Pub. No.: WO2017/187348
PCT Pub. Date: Nov. 2, 2017

(65) Prior Publication Data
US 2019/0134667 A1    May 9, 2019

Related U.S. Application Data

(60) Provisional application No. 62/326,890, filed on Apr. 25, 2016.

(51) Int. Cl.
*B25B 27/14*      (2006.01)
*A61B 17/32*     (2006.01)
(Continued)

(52) U.S. Cl.
CPC ........ *A61B 17/320068* (2013.01); *B06B 3/00* (2013.01); *B25B 27/14* (2013.01); *F16B 5/02* (2013.01); *A61B 2017/00477* (2013.01)

(58) Field of Classification Search
CPC . B25B 25/00; B25B 27/14; F16B 5/02; B06B 3/00
See application file for complete search history.

(56) References Cited

U.S. PATENT DOCUMENTS

2017/0196623 A1 * 7/2017 Nagtegaal .............. A61B 17/29

OTHER PUBLICATIONS

International Search Report; Canadian Intellectual Property Office; International Application No. PCT/IB2017/052388 dated Aug. 8, 2017; 3 pages.

(Continued)

*Primary Examiner* — Daniel J Wiley
(74) *Attorney, Agent, or Firm* — Taft Stettinius & Hollister LLP

(57) ABSTRACT

There is described a device for connecting a first mechanical waveguide and a second mechanical waveguide, including a first body for receiving the first waveguide, and a second body for receiving the second waveguide. The second body includes a tubular member having a first thread extending on an internal surface thereof, a first tubular screw having a second thread on an external surface corresponding to the first thread, and a third thread extending on an internal surface, with a pitch of the second thread being greater than a pitch of the third thread. The second body also includes a second tubular screw having a fourth thread extending on an external surface corresponding to the third thread with the second tubular screw being threadingly and frictionally engaged with the first tubular screw, a triggering member for rotating the first tubular screw, and an indexer for limiting a rotation of the second tubular screw to at least an initial angular position.

20 Claims, 10 Drawing Sheets

(51) Int. Cl.
*B06B 3/00* (2006.01)
*F16B 5/02* (2006.01)
*A61B 17/00* (2006.01)

(56) References Cited

OTHER PUBLICATIONS

Written Opinion of the International Searching Authority; Canadian Intellectual Property Office; International Application No. PCT/IB2017/052388; dated Aug. 8, 2017; 3 pages.

* cited by examiner

CONNECTOR DEVICE FOR CONNECTING MECHANICAL WAVEGUIDES

CROSS REFERENCE TO RELATED APPLICATIONS

This application is a U.S. National Phase of International PCT Application No. PCT/IB2017/052388 filed Apr. 25, 2017, which claims the benefit of U.S. Provisional Application No. 62/326,890 filed Apr. 25, 2016, the contents of each application hereby incorporated by reference in their entirety.

TECHNICAL FIELD

The present invention relates to the field of connectors, and more particularly to connectors for mechanical waveguides.

While connecting two elements together, it may be required to build a large pre-load between two elements, e.g. bolts and nuts, and an external tool, e.g. a wrench, is usually used by a user to connect the two elements together while building the pre-load. However, in some instances, it may not be possible or advisable to use an external tool. For example, for the connection of a disposable element on a medical device, it may be advantageous that the connector for connecting the disposable element to the medical device comprises a built-in mechanism that provides a large mechanical advantage to the user so that the force required to create the connection be reasonable.

Mechanisms providing a large mechanical advantage, e.g. fine pitch threads, levers, inclines, etc., transduce a large required output force (and small displacement) into a large input displacement (and small input force), or vice versa. However, in some instances, it may be required to have a high mechanical advantage solely at the end of the connection process while a large displacement may be required at the beginning of the connection process. These requirements may appear contradictory. For example, a thread would require having a variable pitch to provide such a feature, and a variable pitch thread requires high precision tooling and may be difficult to implement.

For example, a connector may be required for connecting together two mechanical waveguides in order to propagate mechanical waves from a wave generator to a patient. In this case and in order to prevent the two mechanical waveguides from being separated due to the vibrations caused by the propagation of the mechanical waves, a pre-load must be build. In order to build the pre-load, it may be advantageous to have a large displacement at the beginning of the connection process to close the initial gap between the two mechanical waveguides and a large force at the end of the connection process to build the required pre-load preventing the waveguides from separating. While complex and cost expensive connection devices may be used for fulfilling those requirements, a connector that would be simple and easy to use would be needed.

Therefore, there is a need for an improved connector device.

SUMMARY

In accordance with a broad aspect, there is provided a connector for connecting together a first mechanical waveguide and a second mechanical waveguide, comprising: a first guide support body for receiving the first mechanical waveguide; and a second guide support body for receiving the second mechanical waveguide, the second guide support body comprising: a tubular member having a fixed position relative to the first guide support body and positioned so that the first and second mechanical waveguides face each other when received on the first and second guide receiving bodies, respectively, the tubular member comprising a first thread extending on an internal surface thereof; a first tubular screw having a second thread extending on an external surface thereof and corresponding to the first thread, the first tubular screw being threadingly engaged into the tubular member and having a third thread extending on an internal surface thereof, a pitch of the second thread being greater than a pitch of the third thread; and a second tubular screw having a fourth thread extending on an external surface thereof and corresponding to the third thread, the second tubular screw having a guide receiving hole extending along a length thereof for receiving the second mechanical waveguide herein, and being threadingly and frictionally engaged with the first tubular screw; a triggering member for rotating the first tubular screw, the triggering member being rotatable between a first position corresponding to an opening of the connector and a second position corresponding to a closing of the connector; and an indexer for limiting a rotation of the second tubular screw to at least an initial angular position, wherein during an initial movement of the triggering member from the initial position to the final position, the second tubular screw has a fixed position relative to the first tubular screw and the first tubular screw rotates and translates within the tubular member towards the first guide support body, wherein during a further movement of the triggering member from the initial position to the final position, the second tubular screw stops rotating while the first tubular screw continues rotating and translating within the tubular member towards the first guide support body to connect together the first and second mechanical waveguides, an angular shift being created between an angular position of the first tubular screw and a position of the second tubular screw once the second tubular screw stops rotating, wherein during an initial movement of the triggering member from the final position to the initial position, the second tubular screw has a fixed position relative to the first tubular screw and the first tubular screw rotates and translates within the tubular member away from the first guide support body, thereby disconnecting the first and second mechanical waveguide, and wherein during a further movement of the triggering member from the final position to the initial position, the indexer stops a rotation of the second tubular screw when at the initial angular position and the first tubular screw continues rotating within the tubular member.

In one embodiment, the connector further comprises a friction element for creating a predefined friction force between the first and second tubular screws.

In one embodiment wherein the second tubular screw comprises at least one friction hole and the friction element comprises at least one ball-nose spring plunger each inserted into a respective one the at least one friction hole, the at least one ball-nose spring plunger abutting against the external surface of the first tubular screw for creating the predefined friction force.

In one embodiment, the triggering device comprises a triggering handle secured to the first tubular screw for rotating the first tubular screw.

In one embodiment, the indexer is further adapted to limit the rotation of the second tubular screw to a final angular position.

In one embodiment the indexer comprises a tubular body inserted over the second tubular screw and having a fixed position relative to the first guide receiving body, and the second tubular screw comprises a tooth projecting from an external surface thereof.

In one embodiment, the tubular body comprises a recess extending between a first end and a second end along a section of a circumference thereof for receiving therein the tooth, the first end being positioned to correspond to the initial angular position of the second tubular screw so that the second tubular screw stops rotating when the tooth abuts the first end.

In one embodiment, the second end of the recess is positioned so that the tooth abuts against the second end while the triggering device moves from the initial position to the final position to stop the rotation of the second tubular screw.

In one embodiment, the tubular body comprises a circumferential aperture extending between a first end and a second end along a section of a circumference thereof for receiving therein the tooth, the first end being positioned to correspond to the initial angular position of the second tubular screw so that the second tubular screw stops rotating when the tooth abuts the first end.

In one embodiment, the second end of the circumferential aperture is positioned so that the tooth abuts against the second while the triggering device moves from the initial position to the final position to stop the rotation of the second tubular screw.

In one embodiment, the connector further comprises a torque limiting device integrated in the triggering device.

In one embodiment, the connector further comprises a connection plate positioned between the first and second waveguide support bodies, the first waveguide support body and the tubular member of the second waveguide body being secured to the connection plate.

In one embodiment, the connection plate comprises a first aperture, the first and second waveguide support bodies being positioned so that the first and second mechanical waveguides face the first aperture.

In one embodiment, the connection plate further comprises a hemi-circular aperture.

In one embodiment, the triggering device comprises a connection section having a first end secured to the first tubular screw and extending through the hemi-circular aperture of the connection plate, the triggering device further comprising a handle section secured at a second end of the connection section.

In one embodiment, the first and second waveguide support bodies each comprises an abutment wall for abutting a flange of the first and second mechanical waveguides, respectively, to prevent a translation of the first and second mechanical waveguides away from one another.

In one embodiment, the first waveguide support body comprises an arm section adapted to receive and align therein the first mechanical waveguide.

In one embodiment, the first waveguide support body further comprises a circular plate provided with a plate notch for insertion of the first mechanical waveguide.

In one embodiment, the first waveguide support body further comprises a hemi-spherical section provided with a section notch for insertion of the first mechanical waveguide.

In one embodiment, the connector further comprises a hemi-circular cap secured to the triggering device for covering the plate and section notches when the triggering device is in the second position.

For the purpose of the present description, a mechanical wave should be understood as a signal having arbitrary amplitude, duration, waveform, frequency, and/or the like. For example, a mechanical wave may have a high/low amplitude, a short/long duration, different waveforms, and any frequency content.

For the purpose of the present description, a mechanical pulse should be understood as a short duration mechanical wave. The duration of a mechanical pulse is of the order of $1/fc$, where fc is the central frequency of the mechanical pulse, which is typically around 500 kHz, and typically within the range 100 kHz to 1 MHz or more generally from 20 kHz to 5 MHz.

Furthermore, a mechanical waveguide should be understood as a waveguide adapted to propagate mechanical waves or pulses along its length. In the present description, the expressions "waveguide", "mechanical waveguide" and "transmission member" may be used interchangeably. The shape and dimension of a waveguide may vary. For example, a waveguide may have a cylindrical shape. The diameter of the waveguide may be constant along its length. Alternatively, the diameter of the waveguide may vary along its length. For example, the diameter of a waveguide may decrease along its length so that the waveguide corresponds to a taper.

For the purpose of the present description, a transmission member should be understood as a waveguide adapted to propagate mechanical pulses or waves. The characteristics such as the shape, the dimensions, the material of which the transmission member is made, and/or the like may vary as long as mechanical waves and pulses may propagates along the transmission member. For example, a transmission member may have a cylindrical shape. The diameter of the cylindrical transmission member may be substantially constant along the longitudinal axis thereof. In another example, the diameter of the cylindrical transmission member may along the longitudinal axis thereof so as to correspond to a taper for example. In an example, a transmission member may be a dispersive waveguide. Alternatively, a transmission member may be non-dispersive.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
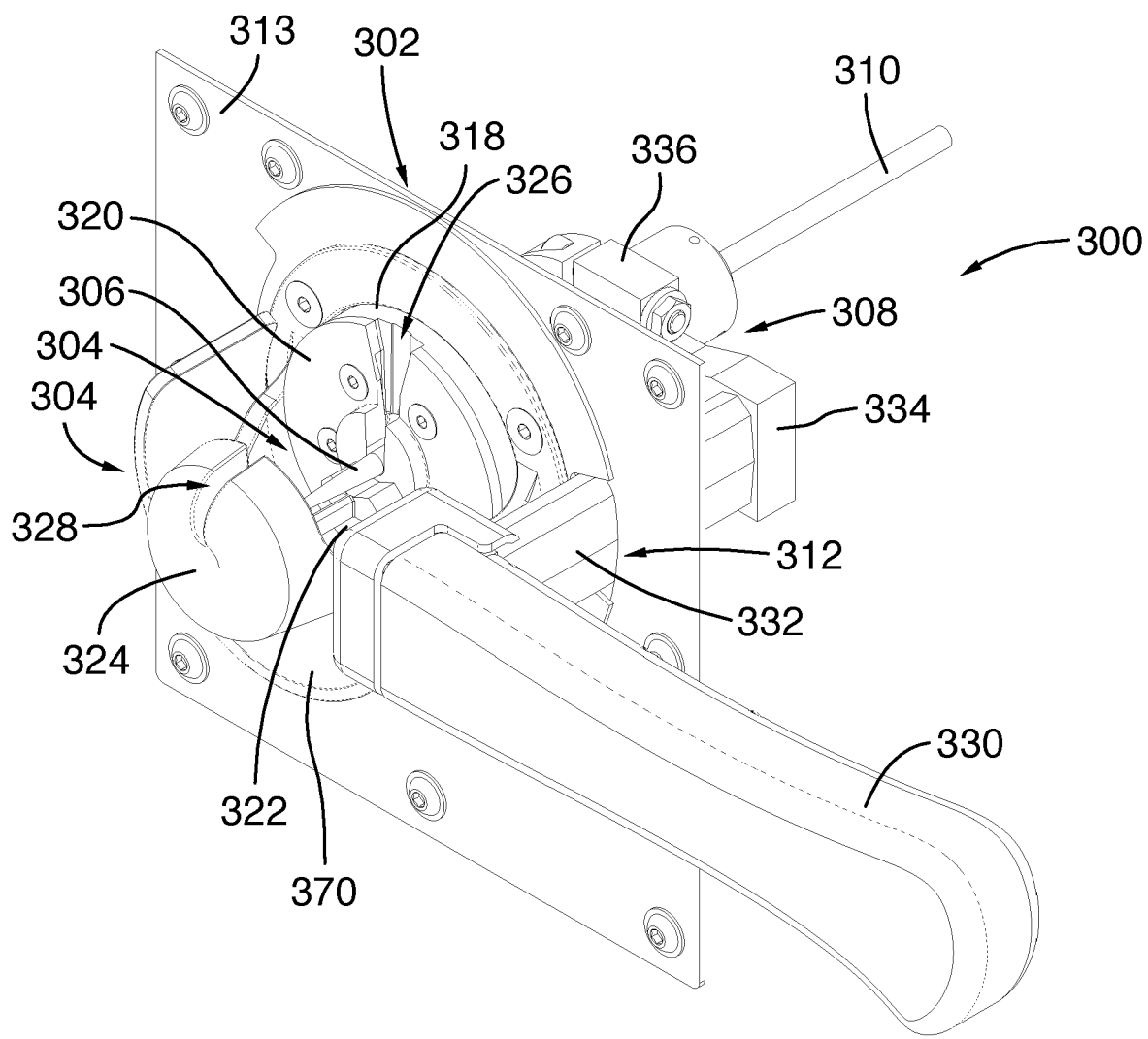
FIG. 1 is a front perspective view of a connector comprising a handle in a horizontal position corresponding to an open configuration for the connector, in accordance with an embodiment.

In the following, there is described a connector for removably connecting together two mechanical waveguides and propagating mechanical waves or pulses between the two waveguides. For example, the connector may be used for removably connecting together two transmission members together or a transmission member and a taper.

As described in further detail below, the connector comprises a frame having an aperture extending therethrough, a first waveguide supporting body for supporting a first mechanical waveguide, a second waveguide supporting body for supporting a second mechanical waveguide, a triggering body for opening and closing the connector and an indexer. The first waveguide supporting body is fixedly secured to the frame on a first side thereof so that the first waveguide, when received in the first waveguide supporting body, faces the aperture of the frame and has a fixed position relative to the frame. The second waveguide supporting body comprises a tubular member extending around the aperture on the second side of the plate and having an internal thread provided with a first pitch. The second waveguide supporting body also comprises a first or outer tubular screw positioned within and threadingly engaged with the tubular member via an outer thread that extends on the outer surface of the first tubular screw. The pitch of the outer thread of the first tubular screw corresponds to the first pitch of the thread of the tubular member. The first tubular screw is further provided with a second or inner thread on its internal surface. The inner thread of the first tubular screw is provided with a second pitch that is less than the first pitch. The second waveguide supporting body further comprises a second or inner tubular screw which is adapted to receive the second mechanical waveguide. The second tubular screw is positioned within the first screw and threading and frictionally engages the first tubular screw. The second tubular screw is provided with an outer thread on its outer surface that matches the inner thread of the first screw. The triggering body is adapted to rotate the first tubular screw and is rotatable between a first or initial angular position corresponding to an open position for the connector and a second or final angular position corresponding to a closed position for the connector.

In order to removably connect together the first and second mechanical waveguides, the first mechanical waveguide is positioned within the first waveguide supporting body and the second mechanical waveguide is positioned within the second screw of the second waveguide supporting body. In one embodiment, the first mechanical waveguide is fixedly secured to the waveguide supporting body and the second mechanical waveguide is fixedly secured to the second screw of the second waveguide supporting body. It should be understood that any adequate means for fixedly securing the first and second mechanical waveguides to the first and second waveguide supporting bodies may be used.

In another embodiment, when received in the first waveguide supporting body, the first mechanical waveguide cannot translate with respect to the first waveguide supporting body in a direction opposite to the second waveguide supporting body. Similarly, when received in the second waveguide supporting body, the second waveguide cannot translate with respect to the second waveguide supporting body in a direction opposite to the first waveguide supporting body. For example, the end of the first mechanical waveguide to be connected to the second mechanical waveguide may be provided with a flange that protrudes radially and is adapted to abut against a wall of the first waveguide supporting body in order to prevent any translation of the first mechanical waveguide in a direction opposite to the second waveguide supporting body. Similarly, the end of the second mechanical waveguide to be connected to the first mechanical waveguide may be provided with a flange that protrudes radially and is adapted to abut against a wall of the second waveguide supporting body (such as the end of the second tubular screw) in order to prevent any translation of the second mechanical waveguide in a direction opposite to the first waveguide supporting body.

In order to insert the mechanical waveguides in their respective waveguide supporting body, the triggering device is positioned in its first angular position and the first and second tubular screw are each in their initial angular position. Once they are positioned within their respective waveguide supporting body, the first and second mechanical waveguides face one another. A gap having a predefined length is then present between the first and second mechanical waveguides. In order to bring together the two mechanical waveguides into physical contact, the triggering body is rotated according to a first rotation direction. During the initial rotation of the triggering body according to the first rotation direction from its initial angular position, the first tubular screw rotates within the tubular member and translates towards the first waveguide supporting body at a first advanced ratio which is defined by the pitch of the first thread. Since it is frictionally secured to the first tubular screw via a predefined friction force between the first and second tubular screws, the second tubular screw also translates towards the first waveguide supporting body at the same pace as the first tubular screw. As a result of the translation of the first and second tubular screws, the second mechanical waveguide moves towards the first mechanical waveguide. When the second mechanical waveguide abuts against the first mechanical waveguide, the first mechanical waveguide exerts on the second mechanical waveguide, a pushing force directed towards the second mechanical waveguide. This pushing force results in a friction force exerted on the second tubular screw. When the friction force exerted on the second tubular screw becomes greater than the predefined friction force between the first and second screws, the second screw stops rotating within the first tubular screw while a further rotation of the triggering device continues rotating the first tubular screw. As a result, the first tubular screw continues moving towards the first waveguide supporting body while the second screw moves away from the first waveguide supporting body relative to the first tubular screw. Since the pitch of the outer surface of the first tubular screw is greater than that of the inner surface of the first tubular screw, the absolute movement of the second tubular screw is a translation towards the first waveguide supporting body but at a reduced advanced ratio in comparison to the advanced ratio of the first tubular screw. The reduced advanced ratio is defined by the difference between the pitch of the outer surface of the first tubular screw and that of the inner surface of the first tubular screw. The triggering device is then rotated up to its second angular position. This allows building a predefined pre-load between the two mechanical waveguides in order to prevent the two waveguides from being separated during the propagation of mechanical pulses between the two mechanical waveguides. The first and second mechanical waveguides are then connected together and mechanical waves or pulses may propagate between the two mechanical waveguides.

In one embodiment, the rotation of the second tubular screw may be stopped before the friction force exerted on the second tubular screw becomes greater than the predefined friction force between the first and second screws. This may be performed by the indexer as described below. Similarly to the above described case, an initial rotation of the triggering device from its initial angular position triggers the translation of the first and second tubular screws at a first advanced ratio. When the triggering device reaches a given angular position which is located between the first and second angular positions, the indexer stops the rotation of the second tubular screw and the second tubular screw translates at the reduced advanced ratio until the triggering device reaches its second angular position.

It should be understood that, the first and second tubular screws have the same angular position at all time during the initial rotation of the triggering device before the rotation of the second screw be stopped since the second tubular screw is frictionally secured to the first tubular screw. However, when the rotation of the second tubular screw is stopped by either the indexer of the friction force applied on the second tubular force, an angular shift is generated between the angular positions of the first and second tubular screws since the first tubular screw continues rotating during the further rotation of the triggering device. The purpose of the indexer is to eliminate the created angular shift when the triggering device is rotated back so its initial angular position so that the first and second tubular screw are brought back to their initial angular position when the triggering device reaches its initial angular position.

In order to disconnect the two mechanical waveguides, the triggering device is rotated from its final angular position in a second rotation direction that is opposite to the first rotation direction. During an initial rotation of the triggering device, the first and second tubular screws are frictionally secured together and translate away from the first waveguide supporting body at the same advanced ratio. The indexer stops the rotation of the second tubular screw before the triggering device reaches its initial angular position. When the indexer stops the rotation of the second tubular screw, the second tubular screw occupies its initial or first angular position. However, the first tubular screw does not occupy its initial angular position yet due to the angular shift between the angular positions of the first and second tubular screws generated during the closing of the connector. When the rotation of the second tubular screw is stopped by the indexer, a further rotation of the triggering device towards its initial angular position triggers a rotation of only the first tubular screw which reduces the angular shift between the angular positions of the first and second tubular screws. When the triggering device reaches its initial angular position, the first tubular screw also reaches its initial angular position and the angular shift between the angular positions of the first and second tubular screws is eliminated. The connector may then be used for connecting again the first and second mechanical waveguides or other mechanical waveguides.

In one embodiment, the connector may comprise a device for adjusting the predefined friction force between the first and second tubular screws.

Figure 2:
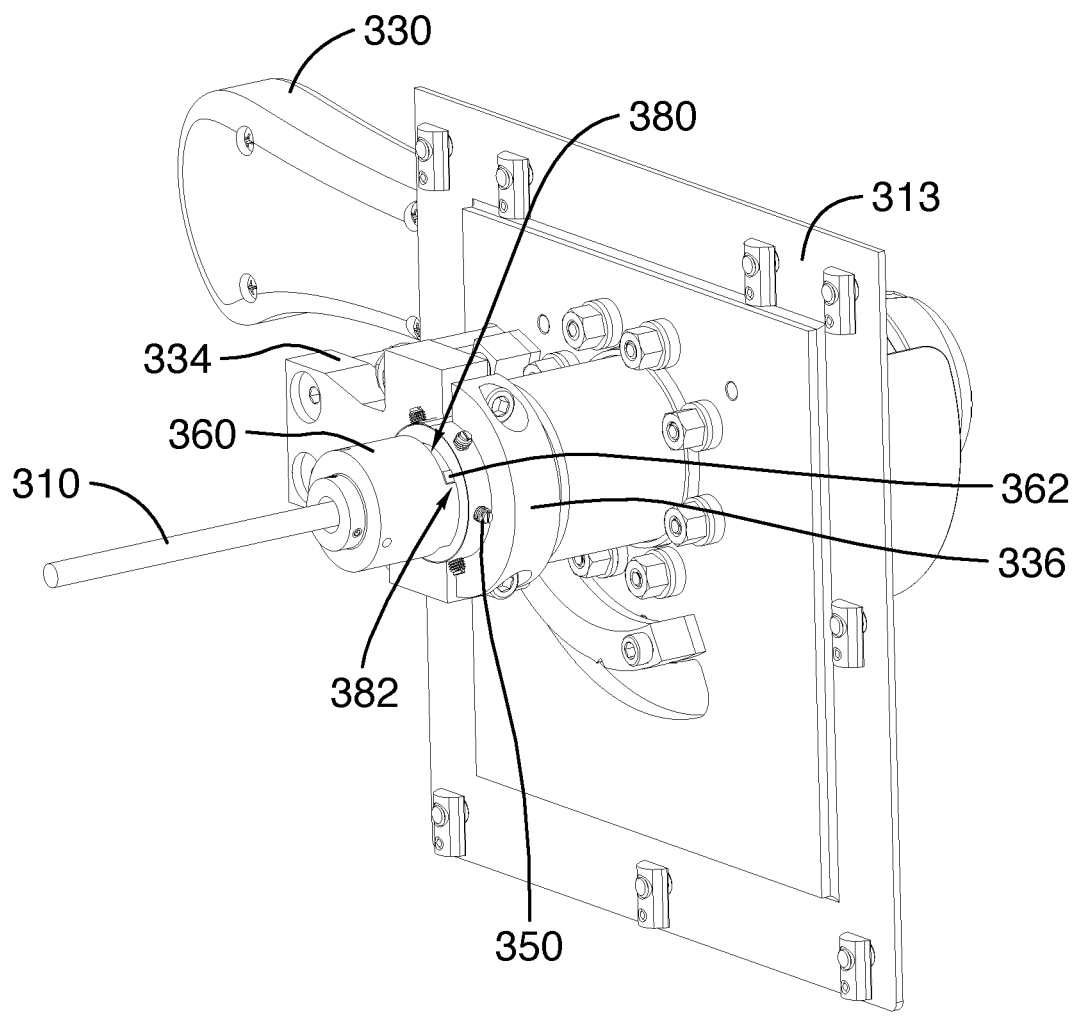
FIG. 2 is a rear perspective view of the connector of FIG. 1 with the handle in the horizontal position.
Figure 3:
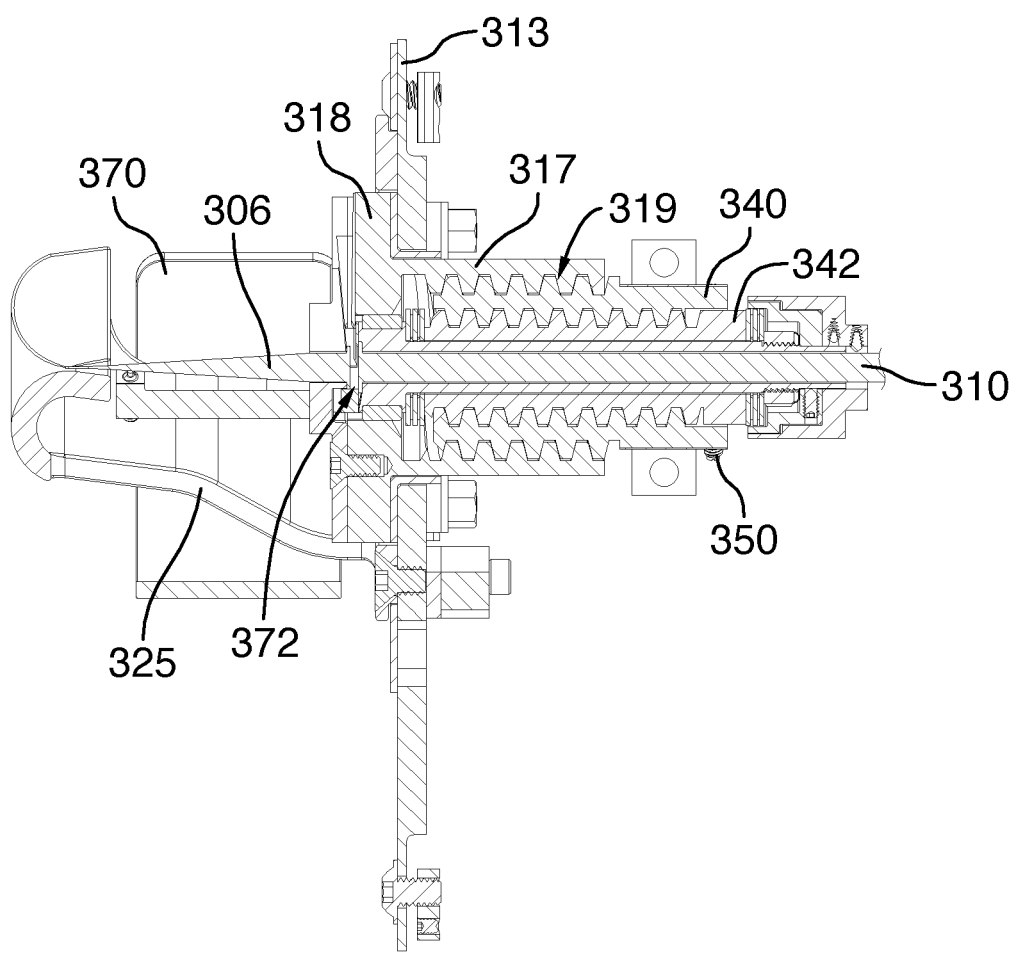
FIG. 3 is a cross-sectional side view of the connector of FIG. 1 with the handle in the first horizontal position.

FIG. 1-3 illustrate one exemplary connector 300 for connecting mechanical waveguides. The connector 300 comprises a frame 302, a first waveguide supporting body 304 for supporting a first mechanical waveguide 306, a second mechanical waveguide supporting body 308 for supporting a second waveguide 310, and a triggering body 312.

Figure 4:
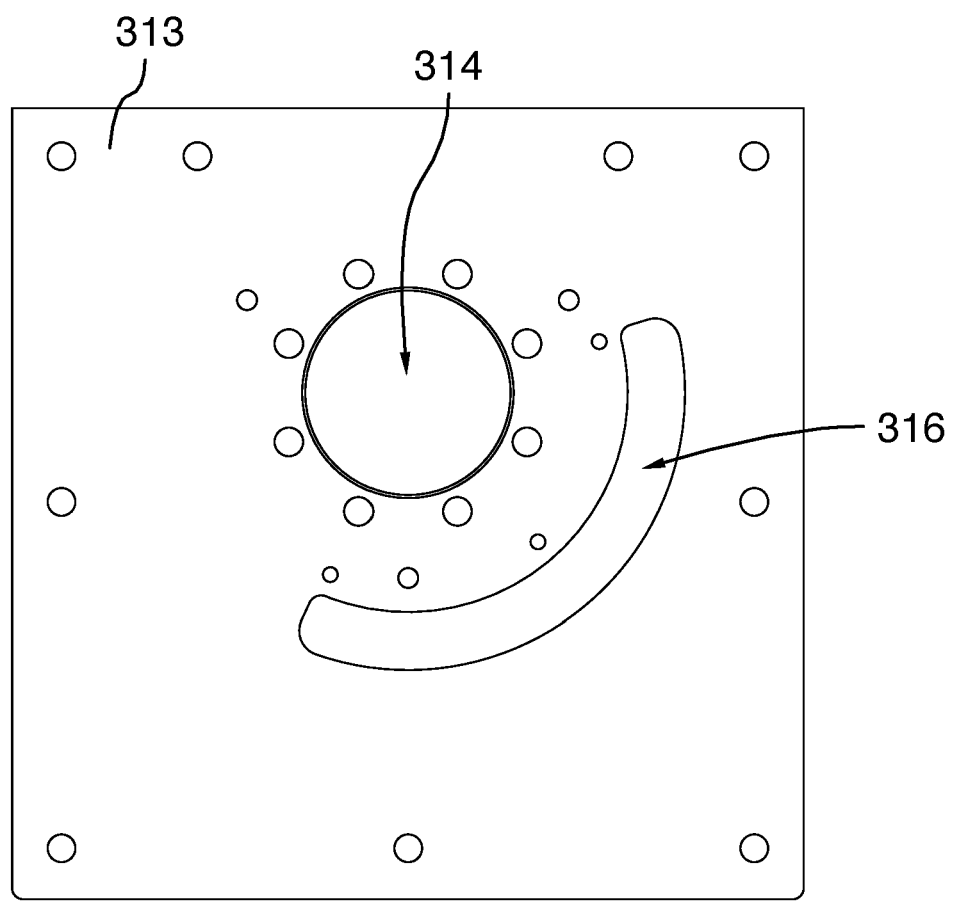
FIG. 4 is a front view of a plate contained in the connector of FIG. 3, in accordance with an embodiment.

As illustrated in FIG. 4, the frame 302 comprises a plate 313 having a circular aperture 314 and a hemi-circular aperture 316, which both extend through the frame 302.

Referring back to FIGS. 1-3, the first waveguide supporting body 304 comprises a circular plate 320, an arm section 322, and a hemi-spherical section 324. The circular plate 320 is fixedly secured to the flange 318 of the tubular member 317 and faces the aperture 314 thereof illustrated in FIG. 4. The circular plate 320 is provided with a notch 326 and a central aperture for inserting the first mechanical waveguide 306. The arm section 322 projects away from the circular plate 320 in a direction opposite to the plate 312 and the hemi-spherical section 324 is secured to plate 312 via an arm 325. The hemi-spherical section 324 is positioned as so to face the arm section 322. The hemi-spherical section 324 is provider with a notch 328 for allowing insertion of the first waveguide. The notches 326 and 328 are aligned together so as to allow the insertion of the first mechanical waveguide on the arm section 322. When the first mechanical waveguide 306 is positioned on the first waveguide supporting body 304, the flange of the first mechanical waveguide 306 abuts against a wall of the first waveguide supporting body 304 so that no translation of the first mechanical waveguide in a direction opposite to the second waveguide supporting body 308 is possible.

In the illustrated embodiment, the first mechanical waveguide 306 is provided with a flange that radially extends from the end of the first mechanical waveguide to be connected to the second waveguide 310. The diameter of the central aperture of the circular plate 320 is slightly greater than that of the first mechanical waveguide 306 and the notch 326 is designed so that only the flange of the first mechanical waveguide 306 is in contact with the circular plate 320. Since the diameter of the flange of the first waveguide 306 is greater than that of the central aperture of the circular plate, the flange abuts against the circular plate 320 when a translation force is exerted on the first waveguide 306 in a direction opposite to the frame 302. When such a translation force is exerted, the flange of the first mechanical waveguide 306 abuts against the circular plate 320.

It should be understood that the first waveguide supporting body 304 may be modified as long as it may support the first mechanical waveguide 306 and prevent a translation of the first mechanical waveguide 306 away from the second waveguide supporting body 304. For example, the first waveguide supporting body may comprise a waveguide receiving plate secured to the plate 313 so that a first end of the waveguide receiving plate faces the aperture 314. The first mechanical waveguide is positioned on the waveguide receiving plate so that its flange abuts against the first end of the waveguide supporting plate.

The triggering body 312 comprises a handle 330, a protruding arm 332 fixedly secured to the handle 330, a connecting plate 334, and an annular plate 336. The protruding arm 332 is inserted into the aperture 316 and may move along the aperture 316. The protruding arm 332 is fixedly secured to the handle 330 at one end and to the connecting plate 334 at the other end. The connecting plate 334 is fixedly secured to the protruding arm 332 at one end and to the annular plate 336 at the other end. It should be understood that the circular length of the aperture 316 defines the rotation amplitude that may be executed by the handle 330. In the illustrated embodiment, the ends of the aperture 316 are located at positions that are angularly spaced by 90 degrees so that the handle may be moved from a horizontal position to a vertical position. When the handle 330 is rotated, the protruding arm 332 moves within the aperture 316 and the annular plate 336 is rotated, i.e. a rotation of the handle 330 triggers the same rotation of the annular plate 336.

The second waveguide supporting body 308 comprises a tubular member 317 that extends through the aperture 314. The tubular member 317 is provided with a flange 318 that is fixedly secured to the plate 313 on the same side as the first waveguide supporting body 304 and a thread 319 that extends on its internal surface. The second waveguide supporting body 308 also comprises a first tubular screw or body 340 and a second tubular screw or body 342. The first tubular screw 340 comprises a threaded section on its external surface and another section of its external surface is not threaded. The thread of the external threaded section of the first tubular screw 340 matches that of the tubular member 317 and the threaded section of the first screw 340 is threadingly engaged into the tubular member 317. The non-threaded external section of the first tubular screw 340 is inserted into the annular plate 336 and fixedly secured thereto so that a rotation of the annular plate 336 triggers a rotation of the first tubular screw 340. The first tubular screw 340 further comprises an internal thread extending along its internal surface. The pitch of the internal thread of the first tubular screw 340 is chosen so as to be less than that of the external thread of the first tubular screw 340.

The second tubular screw 342 comprises an external thread on its external surface that matches the internal thread of the first tubular screw 340. The second screw 342 comprises an aperture that extends along its entire length that is sized and shaped for receiving the second mechanical waveguide 310 therein. In the illustrated embodiment, the second mechanical waveguide 310 is provided with a flange that extends radially at the end facing the first mechanical waveguide 306. The second mechanical waveguide 310 is positioned within the second tubular screw 342 so that the flange faces the first mechanical waveguide 306 and abuts against the end of the second tubular screw 342.

In one embodiment, the second tubular screw 342 is frictionally secured to the first screw 340 via for example ball-nose spring plungers 350 inserted into holes present along the circumference of the non-threaded section of the first tubular screw 340. The ball-nose spring plungers 350 exert a predefined friction force on the second tubular screw 342 so that a rotation of the first tubular screw 340 triggers the same rotation of the second tubular screw 342.

It should be understood that the ball-nose spring plungers 350 may be replaced by any adequate element that allows creating a predefined friction force between the first and second tubular screws 340 and 342. For example, screws may be used in replacement of the ball-nose spring plungers 350. It should also be understood that any adequate device or combination of devices that allows for the creation of the predefined friction force between the first and second tubular screws may be used.

In one embodiment and as illustrated in FIG. 2, the connector 300 further comprises an indexer body 360 for limiting the rotation of the second screw 342. The indexer body 360 has a fixed position relative to the first waveguide supporting body 304 and is fixedly secured to the plate 313. The indexer body 360 is positioned at the end of the second tubular screw 342 that is opposite to the frame 302. The indexer body 360 has a tubular shape and is inserted around a portion of the end section of the second tubular screw 342. The end of the indexer body 360 that is located around the second tubular screw 342 is provided with a recess 380 that extends along a portion of the circumference thereof between a first end 382 and a second end 384. The second tubular screw 342 is provided with a tooth or protrusion 362 that extends radially and outwardly from its external surface. The tooth 362 is positioned so as to be within the recess of the indexer body 360. When the connector 300 is in the open position, the tooth 362 abuts against the end 382 of the recess 380 and the handle 330 and the first and second tubular screws 340 and 342 are in their respective initial angular position.

In one embodiment, when the connector 300 is in a closed position in which the first and second mechanical waveguides 306 and 310 are connected together, the tooth 362 is located between the first and second ends 382 and 384 of the recess 380.

In another embodiment, the tooth 362 abuts against the second end 384 of the recess 380 of the indexer body 360 when the connector is in the closed position.

In one embodiment, the triggering device 312 is provided with a hemi-circular cap 370 which is secured to the handle 330.

FIGS. 1-3 and 5 illustrate the connector 300 in an open position. In this position, the handle 330 is in a horizontal position and the cap 370 does sot cover the notch 326 of the circular plate 320 so the first mechanical waveguide 306 may be inserted into the first waveguide support body 304. The second mechanical waveguide 310 is also inserted into the second waveguide support body 308, i.e. into the second screw 342. The flange of the second mechanical waveguide 310 then abuts against the second waveguide support body 308 such as against the end of the second tubular screw 342 that faces the first waveguide support body 304. When the connector 300 is in the open position, a gap 372 is located between the first and second mechanical waveguides and the tooth 362 abuts against the first end 382 of the recess 380 of the indexer body 360.

Figure 5:
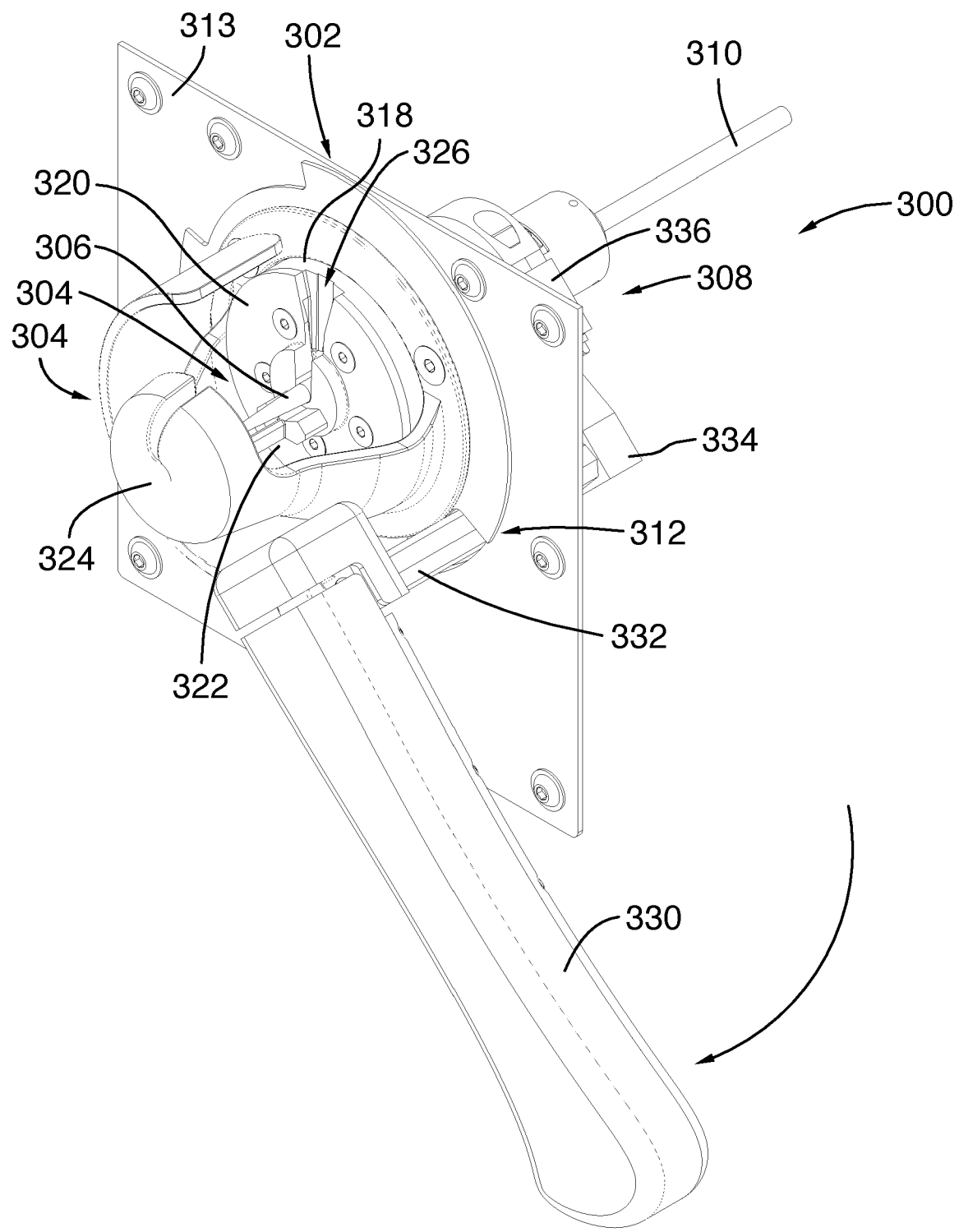
FIG. 5 is a front perspective view of the connector of FIG. 1 with the handle in an intermediary position between the horizontal position and a vertical position, in accordance with an embodiment.
Figure 6:
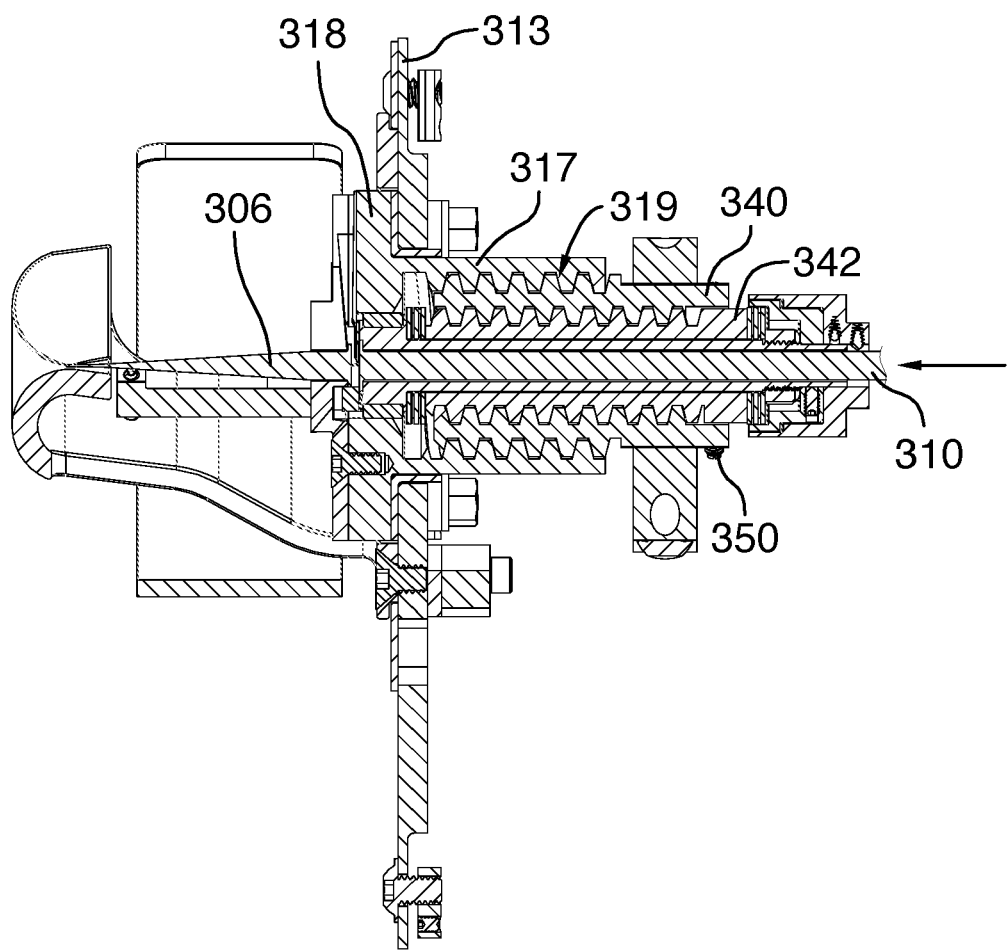
FIG. 6 is a side cross-sectional view of the connecter of FIG. 5.
Figure 7:
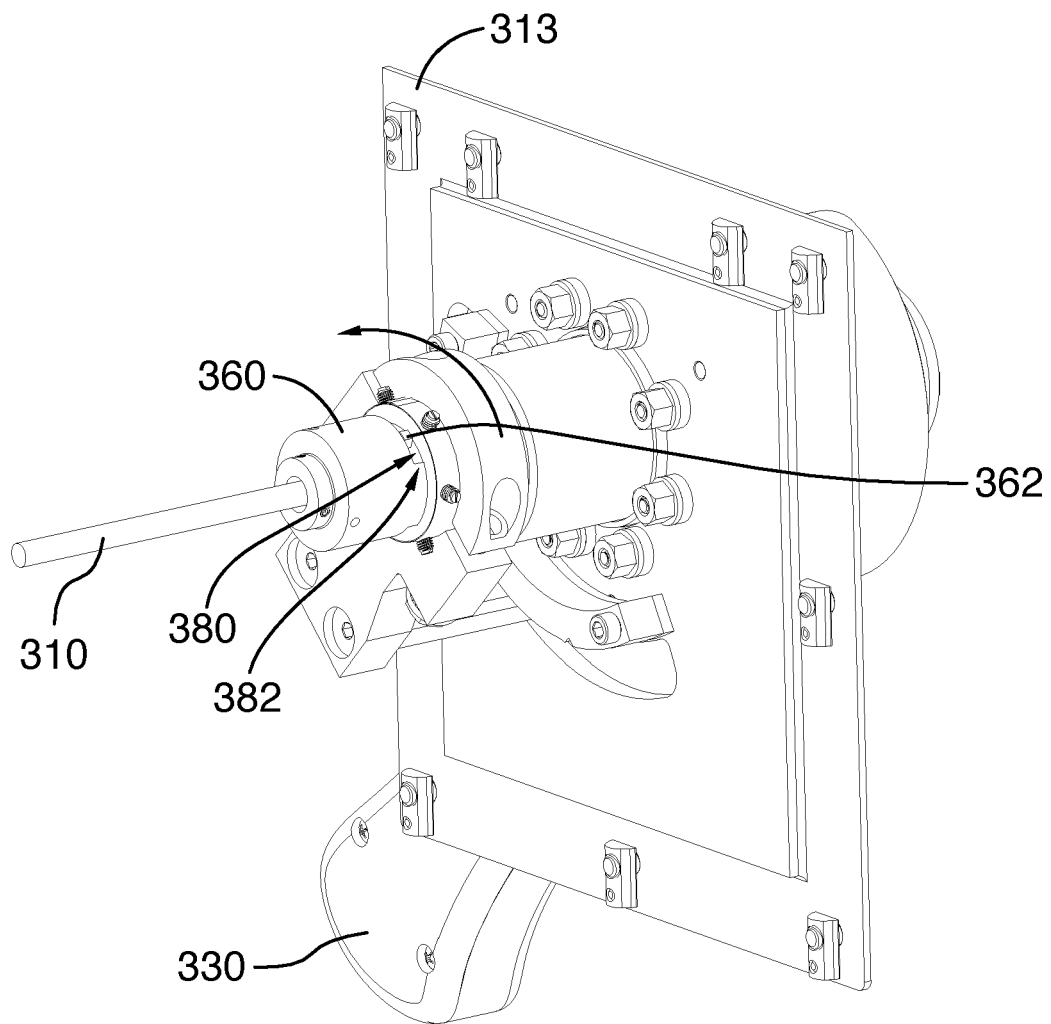
FIG. 7 is a rear perspective view of the connector of FIG. 5.

The connector 300 is closed by rotating the handle 330 clockwise starting from its initial horizontal angular position as illustrated in FIG. 5. The rotation of the handle 330 triggers a rotation of the annular plate 336 which in turns triggers a rotation of the first tubular screw 340 starting from its initial angular position. The rotation of the first tubular screw 342 within the tubular member 317 generates a translation of the first screw 340 towards the first waveguide support body 304 according to a first advanced ratio, as illustrated in FIG. 6. Since it is frictionally secured to the first tubular screw 340, the second tubular screw 342 follows the same rotation as that of the first tubular screw 340. As a result, the second tubular screw 342 and therefore the second mechanical waveguide 310 follow the same translation as that of the first tubular screw 340 towards the first waveguide support body 304 according to the first advanced ratio. The second mechanical waveguide 308 then translates towards the first mechanical waveguide 306 and the gap 372 between the two mechanical waveguides 306 and 310 decreases. During the rotation of the handle 330, the tooth 362 rotates away from the first end 382 of the recess 380 of the indexer body 360 towards the second end thereof, as illustrated in FIG. 7.

Figure 8:
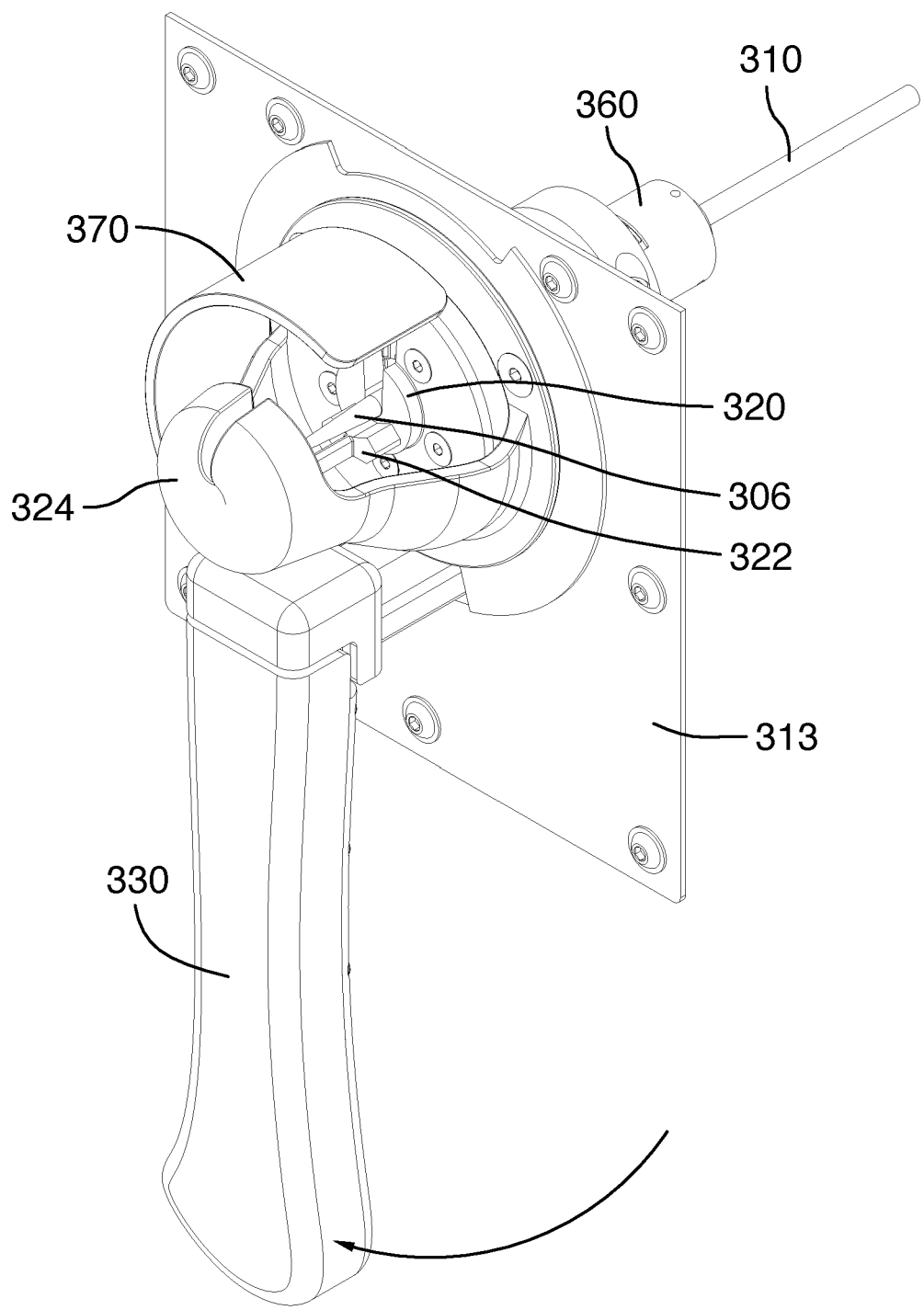
FIG. 8 is a front perspective view of the connector of FIG. 3 with the handle in a position close to the vertical position, in accordance with an embodiment.
Figure 9:
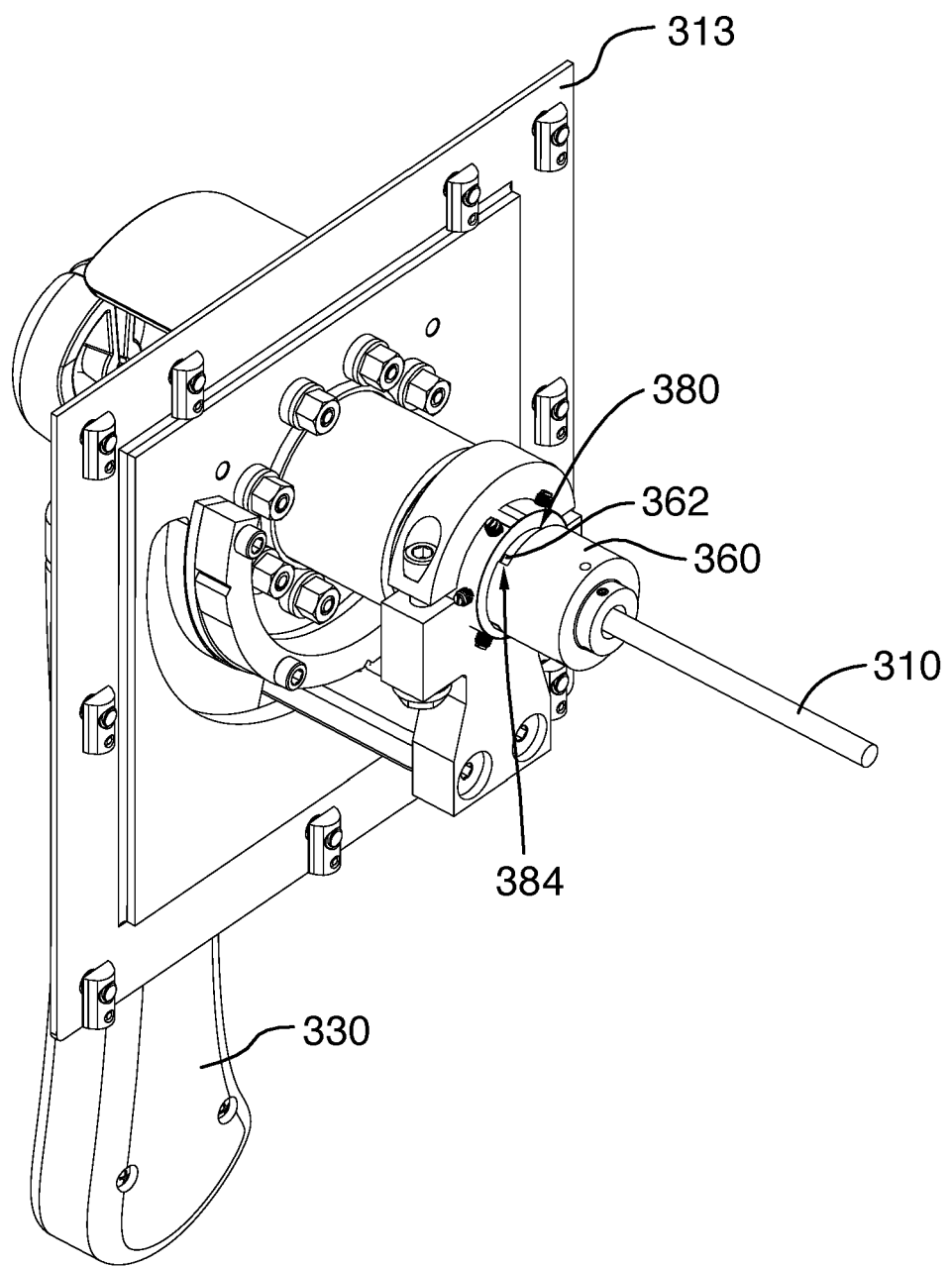
FIG. 9 is a rear perspective view of the connector of FIG. 8.

As the handle 330 approaches its final vertical angular position corresponding to the closed position for the connector 300, as illustrated in FIGS. 8 and 9, the second mechanical waveguide 30 abuts against the first mechanical waveguide 306 which in turn exerts a push force against the second mechanical waveguide 308, thereby connecting together the first mechanical waveguide 306 and the second mechanical waveguide 310. The push force exerted by the first mechanical waveguide 306 on the second mechanical waveguide 310 creates a friction force exerted on the second tubular screw 342.

In one embodiment, the circumferential length of the recess 380 is chosen so that the indexer body stops the rotation of the second tubular screw 342 before the friction force exerted on the second tubular screw 342 becomes greater than the predefined friction force between the first tubular screw 340 and the second tubular screw 342. In this case, the tooth abuts against the second end of the recess 380 during the rotation of the handle 330 when the handle has an angular position located between the horizontal and vertical angular positions.

In another embodiment, the circumferential length of the recess 380 is chosen so that the indexer body does not stop the rotation of the second tubular screw 342. In this case, the tooth does not abut against the second end of the recess 380 during the rotation of the handle 330. The rotation of the second screw is stopped when the friction force exerted on the second tubular screw 342 becomes greater than the predefined friction force between the first tubular screw 340 and the second tubular screw 342. It should be understood that the predefined friction force may be adjusted by adequately choosing the internal diameter of the first tubular screw 340 and the external diameter of the second tubular screw 342. In an embodiment in which the connector 300 comprises at least one ball-nose spring plunger 350, the predefined friction force may be adjusted via the ball-nose spring plunger 350.

Once the rotation of the second tubular screw 342 has been stopped by either the indexer body 360 or the friction force exerted on the second tubular screw 342 and upon further rotation of the handle 330 towards its final angular position, the first screw 340 continues rotating within the tubular member 317 and translating towards the first waveguide support body 304 at the first advanced ratio while the second tubular screw 342 translates relative to the first tubular screw 340 in a direction opposite to the first waveguide supporting body 304. Since the pitch of the outer surface of the first tubular screw 340 is greater than that of the external surface of the second tubular screw 342, the absolute movement of the second tubular screw 342 is a translation towards the first waveguide supporting body 304 but at a reduced advanced ratio in comparison to the advanced ratio of the first tubular screw 340. The reduced advanced ratio is defined by the difference between the pitch of the outer surface thread of the first tubular screw 340 and that of the inner surface thread of the first tubular screw 340. This allows building a pre-load between the two mechanical waveguides 306 and 310. When the triggering device 312 reaches its final angular position, e.g., the vertical position, the maximal and predefined pre-load between the two mechanical waveguides 306 and 310 is reached, thereby preventing the two mechanical waveguides 306 and 310 from being separated during the propagation of mechanical pulses between the two mechanical waveguides 306 and 310. The first and second mechanical waveguides 306 and 310 are then connected together and mechanical waves or pulses may propagate therebetween.

Since they are frictionally secured together during the initial rotation of the first tubular screw 340 via the handle 330, the first and second tubular screws 340 and 342 rotates at the same rotation speed and therefore occupy the same angular position, i.e. there is no shift between the angular positions of the first and second tubular screws 340 and 342. As explained above, an angular shift between the angular positions of the first and second tubular screws is created during the rotation of the handle 330 once the rotation of the second tubular screw 342 is stopped since the first tubular screw 340 continues rotating while the second tubular screw stops rotating. The indexer allows eliminating the angular shift created during the closing of the connector 300 when the connector 300 is subsequently opened.

Figure 10:
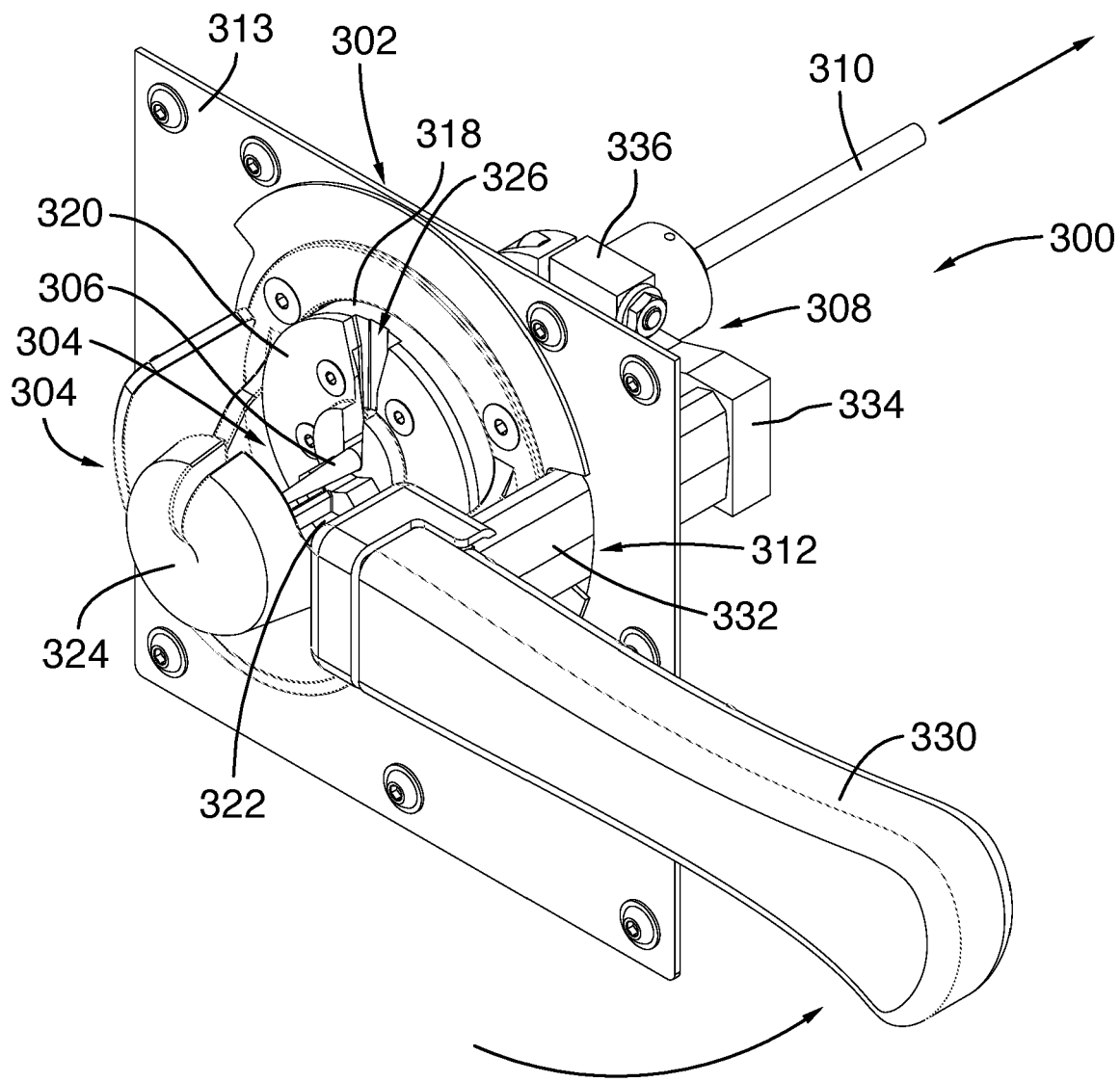
FIG. 10 is a front perspective view of the connector of FIG. 3 when the handle is moved from the vertical position towards the horizontal position, in accordance with an embodiment.

In order to disconnect the first and second mechanical waveguides 306 and 310, the handle 330 is rotated anti-clockwise from its vertical final angular position towards its horizontal initial angular position, as illustrated in FIG. 10. During the initial rotation of the handle 330, the pre-load exerted on the second screw is released and the first and second screws 340 and 342 rotates relative to the tubular body 317 with the second screw 342 having a fixed position relative to the first screw 340 until the tooth 362 abuts against the second end of the recess 380 of the indexer body 360. The abutment of the tooth 362 against the second end of the recess 380 of the indexer body 362 prevents any further rotation of the second tubular screw 342. The second tubular screw 342 is then in its initial angular position that it occupied prior to the closing of the connector 300. Once the tooth 362 abuts against the second end of the recess 380 of the indexer body 360 the first tubular screw 340 continues rotating within the tubular member 317 as the handle 330 is further rotated. When the handle reaches its initial angular position, the rotation of the handle 330 and therefore that of the first tubular screw 340 are stopped. The first tubular screw 340 is then in its initial angular position that it occupied before the closing of the connector 300. Since only the first tubular screw 340 rotates after the tooth 362 abuts against the second end of the recess 360, the further rotation of the handle 330 allows eliminating the angular shift that was created between the angular positions of the first tubular screw 340 and the second tubular screw 342 during the closing of the connector 300. The indexer body 360 allows resetting the first and second screws 340 and 342 to their respective initial angular position.

It should be understood that the angular position of the first end 382 of the recess 380 of the indexer body 360 is chosen so as the tooth 362 abuts against the first end 382 and the second tubular screw 342 be in its initial angular position. In one embodiment, the length of the recess 380 along the circumference of the indexer body 360 or the angular position of the second end of the recess 380 is chosen so that the tooth 362 does not abut against the second end of the recess 380 during the closing of the connector 300. In another embodiment, the length of the recess 380 along the circumference of the indexer body 360 or the angular positon of the second end of the recess 380 is chosen so that the tooth 362 abuts against the second end of the recess 380 during the closing of the connector 300 to stop the rotation of the second tubular screw 342. The angular positions of the ends of the recess 380 then defines the maximal rotation amplitude for the second tubular screw 342 during the opening or closing of the connector 300.

In one embodiment, the present connector 300 allows generating a large pre-load on the two waveguides while a user only applies a substantially small force on the handle 330.

In one embodiment, a coupler such as a coupling fluid or a solid medium may be inserted between the two mechanical waveguides 306 and 310 to promote the transmission of the mechanical waves or pulses between the two mechanical waveguides 306 and 310 and/or provide electrical insulation between the two mechanical waveguides 306 and 310. The coupler may be initially mounted on the first mechanical waveguide 306, the second mechanical waveguide 310, or on both the first and second mechanical waveguides 306 and 310. Alternatively, the coupler may be floating in between the first and second mechanical waveguides 306 and 310 or added at the time of the connection.

It should be understood that modifications may be made to the connector 300. For example, while in the illustrated embodiment the handle 330 rotates by an angle of 90 degrees between a horizontal position and a vertical position, it should be understood that the connector 300 may be designed so that the handle may rotate by more than 90 degrees or less than 90 degrees for connecting and disconnecting the first and second mechanical waveguides 306 and 310 together. In this case, the length of the hemi-circular aperture 316 is then adjusted accordingly. In another example, the location where some elements are secured may vary. While the tubular member 317 is secured to the plate 313 on the side of the first waveguide supporting body 304, it should be understood that the tubular member 317 may be secured on the other side of the plate 313. In this case, the first waveguide supporting body 304 is then secured directly to the plate 313. In a further example, it should be understood that any adequate means for rotating the first screw 340 may be used and this means should not be limited to the illustrated triggering body.

In one embodiment, the connector 300 may further comprise a torque limiting device (not shown) that may be integrated into the handle 330 in order to provide a user with a tactile, visual, and/or sound feedback when the required tightening torque is reached, i.e., when the final angular position of the handle is reached.

It should be understood that some elements of the connector 300 may be modified or omitted. For example, the cap 370 may be omitted. In this case, the handle 330 may be directly secured to the first tubular screw 340 and the protruding arm 332, the connecting plate 334 and/or the annular plate 336 may be omitted. In a further example, the plate 313 may be omitted and the first and second waveguide support bodies 304 and 308 may be secured together. For example, the plate 318 may be omitted and the tubular member 317 may be directly secured to the plate 320. In another example, the ball-nose spring plungers 350 may be omitted.

It should be understood that the indexer body 360 may be modified as long it limits the rotation of the second screw 342. For example, the recess 380 may be replaced with an opening extending along a portion of the circumference of the indexer body 360 and the tooth 362 may be inserted into the opening. As for the recess 380, the angular position of one end of the aperture along the circumference of the indexer body 360 defines the initial angular positon for the second tubular screw 342. The angular position of the second and opposite end of the aperture may be chosen so as to stop the rotation of the second tubular screw 342 when the second tubular screw 342 reaches a predefined angular position.

The embodiments of the invention described above are intended to be exemplary only. The scope of the invention is therefore intended to be limited solely by the scope of the appended claims.

We claim:

1. A connector for connecting together a first mechanical waveguide and a second mechanical waveguide, comprising:
   a first guide support body for receiving the first mechanical waveguide; and
   a second guide support body for receiving the second mechanical waveguide, the second guide support body comprising:
      a tubular member having a fixed position relative to the first guide support body and positioned so that the first and second mechanical waveguides face each other when received on the first and second guide receiving bodies, respectively, the tubular member comprising a first thread extending on an internal surface thereof;
      a first tubular screw having a second thread extending on an external surface thereof and corresponding to the first thread, the first tubular screw being threadingly engaged into the tubular member and having a third thread extending on an internal surface thereof, a pitch of the second thread being greater than a pitch of the third thread; and
      a second tubular screw having a fourth thread extending on an external surface thereof and corresponding to the third thread, the second tubular screw having a guide receiving hole extending along a length thereof for receiving the second mechanical waveguide herein, and being threadingly and frictionally engaged with the first tubular screw;
   a triggering member for rotating the first tubular screw, the triggering member being rotatable between an initial position corresponding to an opening of the connector and a final position corresponding to a closing of the connector; and
   an indexer for limiting a rotation of the second tubular screw to at least an initial angular position,
   wherein during an initial movement of the triggering member from the initial position to the final position, the second tubular screw has a fixed position relative to the first tubular screw and the first tubular screw rotates and translates within the tubular member towards the first guide support body,
   wherein during a further movement of the triggering member from the initial position to the final position, the second tubular screw stops rotating while the first tubular screw continues rotating and translating within the tubular member towards the first guide support body to connect together the first and second mechanical waveguides, an angular shift being created between an angular position of the first tubular screw and a position of the second tubular screw once the second tubular screw stops rotating,
   wherein during an initial movement of the triggering member from the final position to the initial position, the second tubular screw has a fixed position relative to the first tubular screw and the first tubular screw rotates and translates within the tubular member away from the first guide support body, thereby disconnecting the first and second mechanical waveguide, and
   wherein during a further movement of the triggering member from the final position to the initial position, the indexer stops a rotation of the second tubular screw when at the initial angular position and the first tubular screw continues rotating within the tubular member.

2. The connector of claim 1, further comprising a friction element for creating a predefined friction force between the first and second tubular screws.

3. The connector of claim 2, wherein the second tubular screw comprises at least one friction hole and the friction element comprises at least one ball-nose spring plunger each inserted into a respective one of the at least one friction hole, the at least one ball-nose spring plunger abutting against the external surface of the first tubular screw for creating the predefined friction force.

4. The connector of claim 1, wherein the triggering member comprises a triggering handle secured to the first tubular screw for rotating the first tubular screw.

5. The connector of claim 1, wherein the indexer is further adapted to limit the rotation of the second tubular screw to a final angular position.

6. The connector of claim 1, wherein the indexer comprises a tubular body inserted over the second tubular screw and having a fixed position relative to the first guide receiving body, and the second tubular screw comprises a tooth projecting from an external surface thereof.

7. The connector of claim 6, wherein the tubular body comprises a recess extending between a first end and a second end along a section of a circumference thereof for receiving therein the tooth, the first end being positioned to correspond to the initial angular position of the second tubular screw so that the second tubular screw stops rotating when the tooth abuts the first end.

8. The connector of claim 7, wherein the second end of the recess is positioned so that the tooth abuts against the second end while the triggering member moves from the initial position to the final position to stop the rotation of the second tubular screw.

9. The connector of claim 6, wherein the tubular body comprises a circumferential aperture extending between a first end and a second end along a section of a circumference thereof for receiving therein the tooth, the first end being positioned to correspond to the initial angular position of the second tubular screw so that the second tubular screw stops rotating when the tooth abuts the first end.

10. The connector of claim 9, wherein the second end of the circumferential aperture is positioned so that the tooth abuts against the second end while the triggering member moves from the initial position to the final position to stop the rotation of the second tubular screw.

11. The connector of claim 1, further comprising a torque limiting device integrated in the triggering member.

12. The connector of claim 1, further comprising a connection plate positioned between the first and second guide support bodies, the first guide support body and the tubular member of the second guide support body being secured to the connection plate.

13. The connector of claim 12, wherein the connection plate comprises a first aperture, the first and second guide support bodies being positioned so that the first and second mechanical waveguides face the first aperture.

14. The connector of claim 13, wherein the connection plate further comprises a hemi-circular aperture.

15. The connector of claim 14, wherein the triggering member comprises a connection section having a first end secured to the first tubular screw and extending through the hemi-circular aperture of the connection plate, the triggering member further comprising a handle section secured at a second end of the connection section.

16. The connector of claim 1, wherein the first and second guide support bodies each comprise an abutment wall for abutting a flange of the first and second mechanical waveguides, respectively, to prevent a translation of the first and second mechanical waveguides away from one another.

17. The connector of claim 1, wherein the first guide support body comprises an arm section adapted to receive and align therein the first mechanical waveguide.

18. The connector of claim 17, wherein the first guide support body further comprises a circular plate provided with a plate notch for insertion of the first mechanical waveguide.

19. The connector of claim 18, wherein the first guide support body further comprises a hemi-spherical section provided with a section notch for insertion of the first mechanical waveguide.

20. The connector of claim 19, further comprising a hemi-circular cap secured to the triggering member for covering the plate and section notches when the triggering member is in the final position.

* * * * *